(12) United States Patent
Dohil et al.

(10) Patent No.: US 7,994,226 B2
(45) Date of Patent: Aug. 9, 2011

(54) METHODS OF TREATING NON-ALCOHOLIC STEATOHEPATITIS (NASH) USING CYSTEAMINE PRODUCTS

(75) Inventors: Ranjan Dohil, San Diego, CA (US); Jerry Schneider, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/745,504

(22) PCT Filed: Nov. 28, 2008

(86) PCT No.: PCT/US2008/085064
§ 371 (c)(1),
(2), (4) Date: May 28, 2010

(87) PCT Pub. No.: WO2009/070781
PCT Pub. Date: Jun. 4, 2009

(65) Prior Publication Data
US 2010/0303870 A1    Dec. 2, 2010

Related U.S. Application Data

(60) Provisional application No. 60/991,517, filed on Nov. 30, 2007, provisional application No. 61/085,397, filed on Jul. 31, 2008.

(51) Int. Cl.
*A01N 33/08* (2006.01)
(52) U.S. Cl. .............. 514/665; 424/474; 424/477
(58) Field of Classification Search .............. None
See application file for complete search history.

(56) References Cited

U.S. PATENT DOCUMENTS

| | | | | |
|---|---|---|---|---|
| 4,324,743 A | | 4/1982 | Feuer | |
| 4,959,306 A | * | 9/1990 | Kameda et al. .............. | 435/7.92 |
| 5,639,743 A | * | 6/1997 | Kaswan et al. .............. | 514/10.2 |
| 5,668,117 A | | 9/1997 | Shapiro | |
| 6,331,316 B1 | * | 12/2001 | Ullah et al. .................. | 424/482 |
| 6,794,414 B1 | | 9/2004 | Steinman | |
| 7,449,451 B2 | | 11/2008 | Prasad et al. | |
| 2003/0013642 A1 | * | 1/2003 | Adamson et al. ................ | 514/6 |
| 2003/0157191 A1 | | 8/2003 | Kil | |
| 2003/0162747 A1 | | 8/2003 | Kil | |
| 2004/0033985 A1 | | 2/2004 | Chi | |
| 2004/0106591 A1 | | 6/2004 | Pacioretty | |
| 2005/0027015 A1 | | 2/2005 | Chi et al. | |
| 2005/0137125 A1 | | 6/2005 | Chan et al. | |
| 2005/0209441 A1 | | 9/2005 | Lile | |
| 2005/0245433 A1 | | 11/2005 | Chan | |
| 2006/0140906 A1 | | 6/2006 | Chi | |
| 2007/0078113 A1 | | 4/2007 | Roth | |
| 2007/0172514 A1 | | 7/2007 | Chi | |
| 2009/0023632 A1 | | 1/2009 | Adamson et al. | |
| 2009/0076166 A1 | | 3/2009 | Dohil et al. | |

FOREIGN PATENT DOCUMENTS

| | | |
|---|---|---|
| JP | 2004-026716 A | 1/2004 |
| WO | 2003/070020 A1 | 8/2003 |
| WO | 2005/049002 A1 | 6/2005 |
| WO | 2005/063226 A1 | 7/2005 |
| WO | 2005/107730 A2 | 11/2005 |
| WO | 2006/072259 A2 | 7/2006 |
| WO | 2007/121545 A1 | 11/2007 |
| WO | 2008/093764 A1 | 8/2008 |
| WO | 2009/070781 A1 | 4/2009 |

OTHER PUBLICATIONS

Sokal et al., "Glycogenolytic action of mercaptoethylamine," Am. J. Physiol., 1959, pp. 261-264, vol. 196, No. 2.
Bacq et al., "The action of cysteamine on liver glycogen," Arch. Intern. de Physiologie, 1953, pp. 417-418, Vol. LXI, No. 3.
Hanel et al., "The utilization of acetate in rat liver after whole-body roentgen irraditaion," Int. J. Rad. Biol., 1959, pp. 366-371, vol. 4.
Manowska et al., "Liver and Muscle Glycogen Contents and Blood Glucose Concentration after AET Or MEA Treatment of Adult Male Mice," Folia Biologica, 1991, pp. 29-31, vol. 31, No. 1-4.
Manowska et al., "Quantiity of Glycogen in the Liver of 19-Day-Old Foetuses After AET, 5-HT, MEA, Or GSH Treatment of Pregnant Mice on the First Day of Gestation," Acta Physiologica Hungarica, 1988, pp. 51-54, vol. 71, No. 1.
Courrier, "Cortisone Et Sexualite Femelle," Societe Beige D'Endocrinologie, 1954, pp. 1-5, Annales D'Endocrinologies, T. 15, No. 1.
Fischer, P., "Hepatic glycogen, x-rays, and cysteamine," 1954, pp. 134-136.
Karnovsky, "Glycogenolytic effect of 2-mercapto-ethylamine in epiphyseal cartilage," Br J Exp Pathol. Jun. 1961; 42:207-11.
Paoletti et al, "A new hepatic- and irradiation-protective agent, 2-methylpiperazine Dithioformate," 1960, pp. 688-696.
Van Cauwenberge et al, "Carbohydrate metabolism, adrenal cortex, and sulfur radio-protectors," 1954, pp. 645-649.
Angulo et al., "Treatment of nonalcoholic fatty liver : present and emerging therapies," Seminars in Liver Disease, Jan. 1, 2001, pp. 81-88, vol. 21, No. 1.
Castro et al., "Prevention by cystamine of liver necrosis and early biochemical alterations in dicued by carbon tetrachloride," Biochemical Pharmoacology, Jan. 1, 1972, pp. 49-52, vol. 21, No. 1.
Gulbahar et al., "Treatment of non-alcoholic steatohepatitis with N-acetyl cystein," Gastroenterology, Apr. 2000, vol. 118, No. 4, Suppl. 2, Part 2.
Marras, G., "Cysteamine and liver disease due to steatogenous diet," L. Arcispedale S. Anna Di Ferrara, 1955, pp. 639-644, vol. 8, No. 4.
Remmer, H., "Arzneimitteltherapie bei Lebererkrankunge = Drug therapy of liver diseases," Medizinische Monatsschrift Fuer Pharmazeuten, Jun. 1, 1983, pp. 171-177, vol. 6, No. 6.

(Continued)

*Primary Examiner* — Robert A Wax
*Assistant Examiner* — Hasan Ahmed
(74) *Attorney, Agent, or Firm* — Gavrilovich Dodd & Lindsey LLP; Joseph R. Baker, Jr.

(57) ABSTRACT

The disclosure relates, in general, to treatment of fatty liver disorders comprising administering compositions comprising cysteamine products. The disclosure provides administration of enterically coated cysteamine compositions to treat fatty liver disorders, such as non-alcoholic fatty liver disease (NAFLD) and non-alcoholic steatohepatitis (NASH).

25 Claims, 7 Drawing Sheets

OTHER PUBLICATIONS

Thong-Ngam et al., "N-acetylcystein attenuates oxidative stress and liver pathology in rats with non-alcoholic steatohepatitis," World Journal of Gastroenterology, Oct. 1, 2007, pp. 5127-5132, vol. 13, No. 38.

Madlinska, K., Supplementary European Search Report, EP Appl. No. EP 08 85 3916, Sep. 1, 2010.

Cystagon Summary of Product Characteristics, first approved in 1997 and last updated in 2009.

Cystagon European public assessment report (EPAR), 2004.

Bendel-Stenzel et al., "Intravenous delivery of cysteamine for the treatment of cystinosis: association with hepatotoxicity," Pediatr Nephrol. Feb. 2008;23(2):311-5. Epub Aug. 1, 2007.

Brok et al., "Intervensions for paracetamol (adetominophen) overdose (Review)," The Cochrane Collaboration, 2009, Issue 1.

Butler et al., "Pantethine and Cystamien Depelete Cystine from Cystinotic Fribroblasts via Efflux of Cysteamine-Cysteine Mixed Disulfide," J. of Clin. Invest., Aug. 1984, pp. 411-416, vol. 74.

Chang et al., "Therapy of NAFLD; Antioxidants and Cytoprotective Agents," J. Clin. Gastroenterol., Mar. 2006, pp. S51-S60, vol. 40. Suppl 1.

Dohil et al., "Enteric-coated cysteamine for the treatment of paediatric non-alcoholic fatty liver disease," Aliment Pharmacol Ther. May 2011;33(9):1036-44. doi: 10.1111/j.0365-2036.2011. 04626.x. Epub Mar. 13, 2011.

Dohil et al., "Long-term treatment of cystinosis in children with twice-daily cysteamine," J Pediatr. May 2010;156 (5):823-7. Epub Feb. 6, 2010.

Dohil et al., "Twice-daily cysteamine bitartrate therapy for children with cystinosis," J Pediatr. Jan. 2010;156(1):71-75. e1-3. Epub.

Dohil et al., "Understanding intestinal cysteamine bitartrate absorption," J Pediatr. Jun. 2006;148(6):764-9.

Dohil et al., "Esomeprazole therapy for gastric acid hypersecretion in children with cystinosis," Pediatr Nephrol. Dec. 2005;20(12):1786-93. Epub Aug. 24, 2005.

Dohil et al., "The evaluation and treatment of gastrointestinal disease in children with cystinosis receiving cysteamine," J Pediatr. Aug. 2003;143(2):224-30.

Fidler et al., "Pharmacokinetics of cysteamine bitartrate following gastrointestinal infusion," Br J Clin Pharmacol. Jan. 2007;63(1):36-40.

Gangoiti et al., "Pharmacokinetics of enteric-coated cysteamine bitartrate in healthy adults: a pilot study," Br J Clin Pharmacol. Sep. 2010;70(3):376-82.

Kleta et al., "Pharmacological treatmetn of nephropathic cystinosis with cysteamine," Expert Opin. Pharmacother., 2004, pp. 2255-2262, vol. 5, No. 11.

Kleta, Robert, "A Deeper Look Into Cysteamine Abbsorption for the Treatment of Cystinosis," J of Pediatrics, 2006, pp. 718-719, vol. 148, No. 6.

Levtchenko et al., "Strict cysteamine dose regimen is required to prevent nocturnal cystine accumulation in cystinosis," Pediatric Nephrol., 2006, pp. 110-113, vol. 21.

Miners et al., "Mechanism of action of paracetomol protective agents in mice in vivo," Biochemical Pharmacology, 1984, pp. 2995-3000, vol. 33, No. 19.

Shiratori et al., "Evidence for Significant Role of Gastrin in Cysteamine-Induced Hypersecretion of Gastric Acid," J. of Clin. Gastroenterol., 1997, pp. S84-S88, vol. 25.

Thoene et al., "Cystinosis intracellular cystine depletion by aminothiols in vitro and in vivo," J. Clinical Investigation, Jul. 1976, pp. 180-189, vol. 58.

van de Berg et al., "Contribution of Gastrin to Cysteamine-induced Gastric Acid Secretion in Rats," Life Sciences, 1993, pp. 1861-1867, vol. 52, No. 23.

Wang et al., "Cerebral Pet imaging and histological evidence of transglutaminase inhibitor cysteamine induced neuroprotection in transgenic R6/2 mouse model of Huntington's disease," J. of the Neurological Sciences, Apr. 2005, pp. 57-66, vol. 231.

http://www.clinicaltrial.gov/ct2/show/NCT00799578, A Preliminary Study to Evaluate Cysteamine Therapy in Human Subjects With Non-Alcoholic Steatohepatitis, 2010.

http://www.news-medical. net/news/20091012/Results-of-Phase-2a-clinical-trial-of-DR-Cysteamine-announced-by-Raptor-Pharmaceutical.aspx, Results of Phase 2a clinical trial of DR Cysteamine announced by Raptor Pharmaceutical, Oct. 2009.

http://www.raptorpharma.com/dr_cysteamine_nash.html, DR Cysteamine for Non-alcoholic Steatohepatitis (NASH), Sep. 2010.

http://www2.niddk.nih.gov/Research/ScientificAreas/DigestiveDiseases/Clinical/LVCT.htm, Clinical Trials in Liver Diseases, Acute Liver Failure Study Group, Sep. 2010.

European Office Action; EP Application No. 07762690.1, European Patent Office, Mar. 3, 2011.

Dohil et al., "Esomeprazole therapy for gastric acid hypersecretion in children with cystinosis," Pediatr Nephrol. Dec. 2005;20(12):1786-93. Epub Aug. 24, 2005.

Ahmed, Hasan Syed, Office Action, U.S. Patent Publication No. 20090076166A1, United States Patent & Trademark Office, Feb. 1, 2011.

Ahmed, Hasan Syed, Notice of Allowance, U.S. Patent Publication No. 20090076166A1, United States Patent & Trademark Office, May 16, 2011.

Raptor Pharmaceuticals Corp., "Raptor Pharmaceuticals Enters Collaboration Agreement with UC San Diego in Liver Disease," Jul. 16, 2008.

Raptor Pharmaceutical Corp., "DR Cysteamine: Non-Alcoholic Steatohepatitis (NASH)," Rodman & Renshaw 10th Annual Healthcare Conference, Nov. 11, 2008.

Raptor Pharmaceutical Corp., "DR Cysteamine: Non-Alcoholic Steatohepatitis (NASH)," Investor Presenation, Summer 2008.

Raptor Pharmaceutical Corp., "New DR Cysteamine Markets," 26th Annual JP MOrgan Annual Healthcare Conference, Jan. 7-10, 2008.

Raptor Pharmaceutical Corp., "Raptor Pharmaceuticals Corp. Enters Agreements to Advance Clinical Pipeline," http://ir.raptorpharma.com/phoenix.zhtml?c=198466&p=irol-newsArticle&ID=1120014&highlight=nash, Mar. 19, 2008.

Raptor Pharmaceutical Corp., "Raptor Pharmaceuticals Corp. Receives FDA Orphan Drug Designation for Cysteamine in Huntington's Disease," http://ir.raptorpharma.com/phoenix.zhtml?c=198466&p=irol-newsArticle&Id=1163467&highlight=nash, Jun. 9, 2008.

Raptor Pharmaceutical Corp., "Raptor Pharmaceuticals Corp. to Present at BIO 2008 International Convention," http://ir.raptorpharma.com/phoenix.zhtml?c=198466&p=irol-newsArticle&ID=1165084&highlight=nash, Jun. 12, 2008.

Raptor Pharmaceutical Corp., "Raptor Pharmaceuticals Enters Collaboration Agreement with UC San Diego in Liver Disease," http://ir.raptorpharma.com/phoenix.zhtml?c=198466&p=irol-newsArticle&ID=1174736&highlight=nash, Jul. 16, 2008.

Raptor Pharmaceutical Corp., "Raptor Pharmaceuticals Announces Phase 2a Clinical Trial Initiation in Non-Alcoholic Steatohepatitis (NASH)," http://ir.raptorpharma.com/phoenix.zhtml?c=198466&p=irol-newsArticle&ID=1213779&highlight=nash, Oct. 20, 2008.

U.S. National Institutes of Health, "View of NCT00799578; A Preliminary Study to Evaluate Cysteamine Therapy in Human Subjects With Non-Alcoholic Steatohepatitis (NASH)," http://clinicaltrials.gov/archive/NCT00799578/2008_11_30, Nov. 30, 2008.

* cited by examiner

METHODS OF TREATING NON-ALCOHOLIC STEATOHEPATITIS (NASH) USING CYSTEAMINE PRODUCTS

CROSS REFERENCE TO RELATED APPLICATIONS

This application is a U.S. National Stage Application filed under 35 U.S.C. §371 and claims priority to International Application No. PCT/US08/85064, filed Nov. 28, 2008, which application claims priority of U.S. Provisional Appl. No. 60/991,517 filed Nov. 30, 2007, and U.S. Provisional Appl. No. 61/085,397 filed Jul. 31, 2008, the disclosures of each of which are incorporated herein by reference in their entirety.

FIELD OF THE INVENTION

The invention relates in general to materials and methods to treat fatty liver disease using cysteamine products.

BACKGROUND

Fatty liver disease (or steatohepatis) is often associated with excessive alcohol intake or obesity, but also has other causes such as metabolic deficiencies including insulin resistance and diabetes. Fatty liver results from triglyceride fat accumulation in vacuoles of the liver cells resulting in decreased liver function, and possibly leading to cirrhosis or hepatic cancer.

Non-alcoholic fatty liver disease (NAFLD) represents a spectrum of disease occurring in the absence of alcohol abuse. A satisfactory treatment for fatty liver disease, such as NAFLD and NASH is not presently available.

SUMMARY

The disclosure provides a method of treating a subject suffering from fatty liver disease comprising administering a therapeutically effective amount of a cysteamine composition. In one embodiment, the fatty liver disease is selected from the group consisting of non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy. In another embodiment, the total daily dose of cysteamine composition is about 0.5-1.0 g/m$^2$. In yet another embodiment, the cysteamine composition is administered at a frequency of 4 or less times per day (e.g., one, two or three times per day). In one embodiment, the composition is a delayed or controlled release dosage form that provides increased delivery of the cysteamine or cysteamine derivative to the small intestine. The delay or controlled release form can provide a $C_{max}$ of the cysteamine or cysteamine derivative, or a biologically active metabolite thereof, that is at least about 35%, 50%, 75% or higher than the $C_{max}$ provided by an immediate release dosage form containing the same amount of the cysteamine or cysteamine derivative. In yet another embodiment, the delayed or controlled release dosage form comprises an enteric coating that releases the cysteamine composition when the composition reaches the small intestine or a region of the gastrointestinal tract of a subject in which the pH is greater than about pH 4.5. For example, the coating can be selected from the group consisting of polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters. The composition can be administered orally or parenterally. In another embodiment, the method results in improvement in liver fibrosis compared to levels before administration of the cysteamine composition. In yet another embodiment, the method results in a reduction in fat content of liver, a reduction in the incidence of or progression of cirrhosis, or a reduction in the incidence of hepatocellular carcinoma. In one embodiment, the method results in a decrease in hepatic aminotransferase levels compared to levels before administration of the cysteamine composition. In a further embodiment, the administering results in a reduction in hepatic transaminase of between approximately 10% to 40% compared to levels before treatment. In yet another embodiment, the administering results in a reduction in alanine or aspartate aminotransferase levels in a treated patient to approximately 30%, 20% or 10% above normal ALT levels, or at normal ALT levels. In yet other embodiment, the administering results in a reduction in serum ferritin levels compared to levels before treatment with the cysteamine composition. The methods and composition of the disclosure can also include administering a second agent in combination with a cysteamine composition to treat fatty liver disease. The subject can be an adult, adolescent or child.

In one aspect, the disclosure provides a method of treating a patient suffering from fatty liver disease, including NAFLD or NASH, comprising administering a therapeutically effective amount of a composition comprising a cysteamine product. The methods of the disclosure also include use of a cysteamine product in preparation of a medicament for treatment of fatty liver disease, and use of a cysteamine product in preparation of a medicament for administration in combination with a second agent for treating fatty liver disease. Also included is use of a second agent for treating fatty liver disease in preparation of a medicament for administration in combination with a cysteamine product. Further provided are kits comprising a cysteamine product for treatment of fatty liver disease, optionally with a second agent for treating fatty liver disease, and instructions for use in treatment of fatty liver disease. The term "fatty liver disease" may include or exclude NASH.

DETAILED DESCRIPTION

Figure 1:
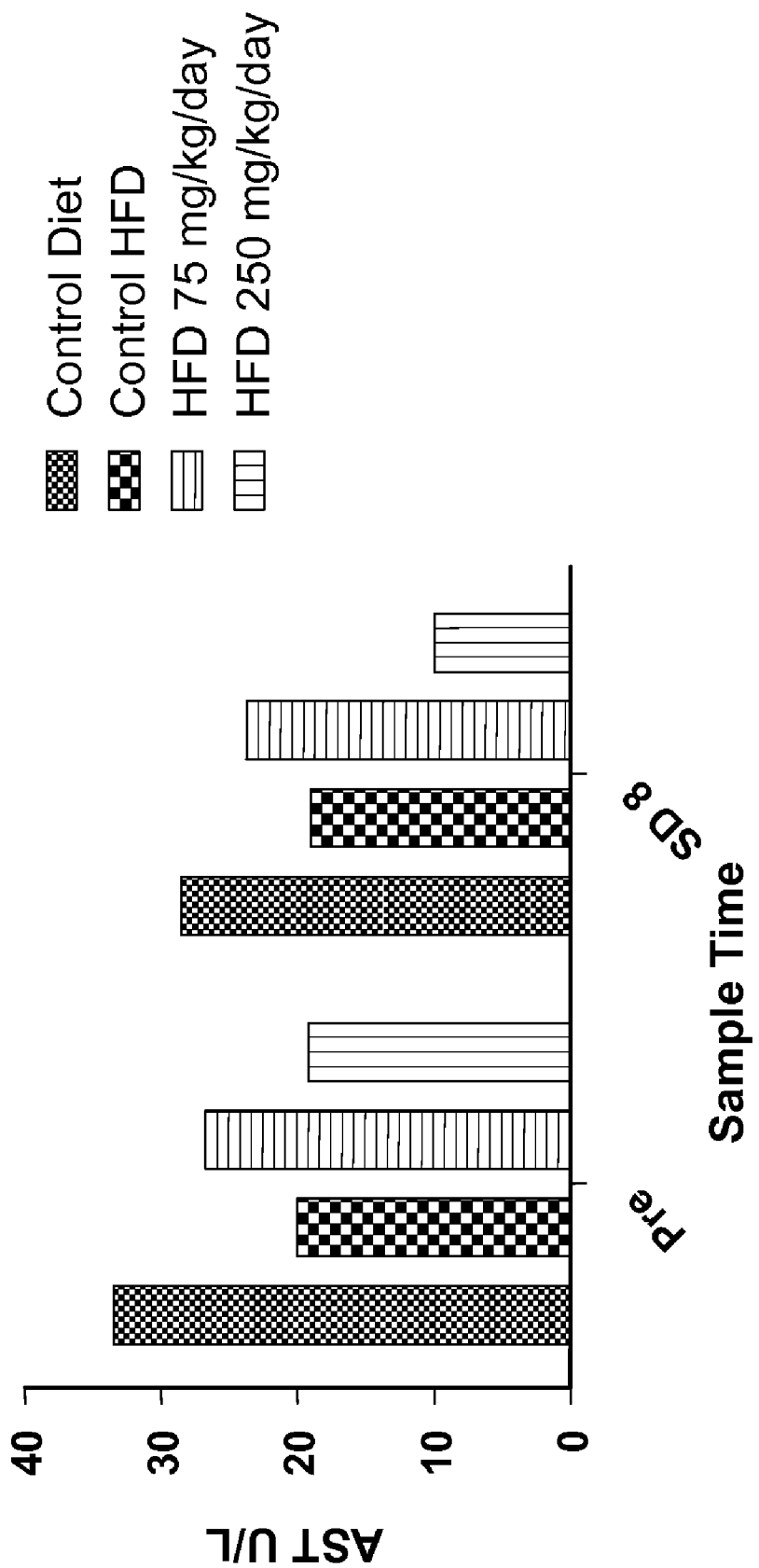
FIG. 1 shows the effect of cysteamine treatment at 0, 75 and 250 mg/kg/day, delivered intraperitoneally, on aspartate aminotransferase (AST) levels in animals fed a high fat diet (HFD) for 8 days. AST levels for control animals, not fed a HFD, are also shown. The graph depicts mean AST values from blood samples collected on study day-1 ("pre") and on study day 8 (SD8).

As used herein and in the appended claims, the singular forms "a," "and," and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The disclosure provides new therapeutics that can alleviate the symptoms associated with fatty liver disease in patients suffering from the disease. The disclosure provides cysteamine compositions which provide an effective therapy for patients in need of treatment.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Cysteamine is a precursor to the protein glutathione (GSH) precursor, and is currently FDA approved for use in the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH synthesis. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a recent study in children with cystinosis, enteral administration of cysteamine resulted in increased plasma cysteamine levels, which subsequently caused prolonged efficacy in the lowering of leukocyte cystine levels (Dohil et al., J Pediatr 2006; 148(6):764-9). This may have been due to "re-cycling" of cysteamine when adequate amounts of drug reached the lysosome. If cysteamine acts in this fashion, then GSH production may also be significantly enhanced.

Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. patent application Ser. No. 11/990,869 and published International Publication No. WO 2007/089670, both claiming priority to U.S. Provisional Patent application No. 60/762,715, filed Jan. 26, 2006, (all of which are incorporated by reference herein in their entirety) showed that cysteamine induced hypergastrinemia arises, in part, as a local effect on the gastric antral-predominant G-cells in susceptible individuals. The data also suggest that this is also a systemic effect of gastrin release by cysteamine. Depending on the route of administration, plasma gastrin levels usually peak after intragastric delivery within 30 minutes whereas the plasma cysteamine levels peak later.

Subjects with cystinosis are required to ingest oral cysteamine (CYSTAGON®) every 6 hours day and night. When taken regularly, cysteamine can deplete intracellular cystine by up to 90% (as measured in circulating white blood cells), and this had been shown to reduce the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration, increases $C_{max}$ and increases AUC. Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

The disclosure provides cysteamine products useful in the treatment of fatty liver diseases and disorders. A cysteamine product refers, generally, to cysteamine, cystamine, or a biologically active metabolite thereof, or combination of cysteamine or cystamine, and includes cysteamine or cystamine salts, esters, amides, alkylated compounds, prodrugs, analogs, phosphorylated compounds, sulfated compounds, or other chemically modified forms thereof, by such techniques as labeling (e.g., with radionuclides or various enzymes), or covalent polymer attachment such as pegylation (derivatization with polyethylene glycol).

A cysteamine product includes cysteamine, cystamine, biologically active metabolites, chemically modified forms of the compound, by such techniques as esterification, alkylation (e.g., C1, C2 or C3), labeling (e.g., with radionuclides or various enzymes), covalent polymer attachment such as pegylation (derivatization with polyethylene glycol) or mixtures thereof. In some embodiments, cysteamine products include, but are not limited to, hydrochloride salts, bitartrate salts, phosphorylated derivatives, and sulfated derivatives. Examples of other cysteamine products include 2-aminopropane thiol-1,1-aminopropane thiol-2, N- and S-substituted cysteamine, AET, aminoalkyl derivatives, phosphorothioate, amifostine (U.S. Pat. No. 4,816,482). In one embodiment, a cysteamine product specifically excludes N-acetylcysteine. In one embodiment, cysteamine products comprise, but are not limited to, structures described below:

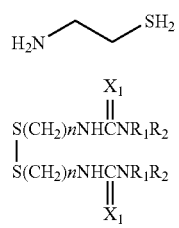

wherein n represents 2 or 3, $R_1$ and $R_2$ each represents a hydrogen atom, or an alkyl group optionally substituted by a hydroxy, amino, alkylamino or dialkylamino group, or represents a cycloalkyl or aryl group, and $X_1$ represents a group selected from the group consisting of =N—CN, =N—NO$_2$, =N—COR$_3$, =N—NR—COOR$_3$, =N—NR—CONH$_2$, =N—SO$_2$R$_3$, =CH—NO$_2$, —CH—SO$_2$R$_3$, =C(CN)$_2$, =C(CN)COOR$_3$ and =C(CN)CONH$_2$, wherein $R_3$ is an alkyl or aryl group. In another aspect, a cysteamine product can comprise a cysteamine radical linked to any number of non-toxic groups as set forth below:

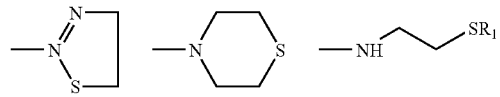

wherein $R_1$ represents hydrogen atom or a straight chain or a branched alkyl group having 1 to 10 carbon atoms.

Pharmaceutically acceptable salts of cysteamine products are also included and comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$^{4+}$) and substituted ammonium (N(R')$^{4+}$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Cysteamine products can be enterically coated. An enterically coated drug or tablet refers, generally, to a drug or tablet that is coated with a substance (an "enteric coating") that remains intact or substantially intact such that the drug or tablet is passed through the stomach but dissolves and releases the drug in the small intestine.

An enteric coating can be a polymer material or materials which encase a medicament core (e.g., cystamine, cysteamine, CYSTAGON® or other cysteamine product). Typically a substantial amount or all of the enteric coating material is dissolved before the medicament or therapeutically active agent is released from the dosage form, so as to achieve delayed dissolution or delivery of the medicament core. A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

The cysteamine product may also include additional pharmaceutically acceptable carriers or vehicles. A pharmaceutically acceptable carrier or vehicle refers, generally, to materials that are suitable for administration to a subject wherein the carrier or vehicle is not biologically harmful, or otherwise, cause undesirable effects. Such carriers or vehicles are typically inert ingredients of a medicament. Typically a carrier or vehicle is administered to a subject along with an active ingredient without causing any undesirable biological effects or interacting in a deleterious manner with any of the other components of a pharmaceutical composition in which it is contained.

A cyteamine product or other active ingredient can comprise a pharmaceutically acceptable salt, ester or other derivative. For example, salts, esters or other derivatives comprise biologically active forms having a similar biological effect compared to a parent compound. Exemplary salts include hydrochloride salt and bistartrate salts.

An active ingredient, pharmaceutical or other composition of the disclosure can comprise a stabilizing agent. Stabilizing agents, generally, refer to compounds that lower the rate at which a pharmaceutical degrades, particularly an oral pharmaceutical formulation under environmental conditions of storage.

As used herein, a "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In one embodiment, a therapeutically effective amount of the cysteamine product ameliorates symptoms, including but not limited to, liver fibrosis, fat content of liver, incidence of or progression of cirrhosis, incidence of hepatocellular carcinoma, increased hepatic aminotransferase levels, such as ALT and AST, increased serum ferritin, elevated levels of gamma-glutamyltransferase (gamma-GT), and elevated levels of plasma insulin, cholesterol and triglyceride.

Non-alcoholic fatty liver disease (NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). NAFLD is linked to insulin resistance, it causes liver disease in adults and children and may ultimately lead to cirrhosis (Skelly et al., J Hepatol 2001; 35: 195-9; Chitturi et al., Hepatology 2002; 35(2):373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). NASH is characterized by the histologic presence of steatosis, cytological ballooning, scattered inflammation and pericellular fibrosis (Contos et al., Adv Anat Pathol 2002; 9:37-51). Hepatic fibrosis resulting from NASH may progress to cirrhosis of the liver or liver failure, and in some instances may lead to hepatocellular carcinoma.

The degree of insulin resistance (and hyperinsulinemia) correlates with the severity of NAFLD, being more pronounced in patients with NASH than with simple fatty liver (Sanyal et al., Gastroenterology 2001; 120(5):1183-92). As a result, insulin-mediated suppression of lipolysis occurs and levels of circulating fatty acids increase. Two factors associated with NASH include insulin resistance and increased delivery of free fatty acids to the liver. Insulin blocks mitochondrial fatty acid oxidation. The increased generation of free fatty acids for hepatic re-esterification and oxidation results in accumulation of intrahepatic fat and increases the liver's vulnerability to secondary insults.

Glutathione (gammaglutamyl-cysteinyl-glycine; GSH) is a major endogenous antioxidant and its depletion is implicated in the development of hepatocellular injury (Wu et al., J Nutr 2004; 134(3):489-92). One such injury is acetaminophen poisoning, where reduced GSH levels become depleted in an attempt to conjugate and inactivate the hepatotoxic metabolite of the drug. After a toxic dose of acetaminophen, excess metabolite (N-acetyl-benzoquinoneimine) covalently binds to hepatic proteins and enzymes resulting in liver damage (Wu et al., J Nutr 2004; 134(3):489-92; Prescott et al., Annu Rev Pharmacol Toxicol 1983; 23:87-101). Increased glutathione levels appears therefore to have some protective effects through the reduction of ROS. Glutathione itself is does not enter easily into cells, even when given in large amounts. However, glutathione precursors do enter into cells and some GSH precursors such as N-acetylcysteine have been shown to be effective in the treatment of conditions such as acetaminophen toxicity by slowing or preventing GSH depletion (Prescott et al., Annu Rev Pharmacol Toxicol 1983; 23:87-101). Examples of GSH precursors include cysteine, N-acetylcysteine, methionine and other sulphur-containing compounds such as cysteamine (Prescott et al., J Int Med Res 1976; 4(4 Suppl):112-7).

Cysteine is a major limiting factor for GSH synthesis and that factors (e.g., insulin and growth factors) that stimulate cysteine uptake by cells generally result in increased intracellular GSH levels (Lyons et al., Proc Natl Acad Sci USA 2000; 97(10):5071-6; Lu S C. Curr Top Cell Regul 2000; 36:95-11).

N-acetylcysteine has been administered to patients with NASH. In reports from Turkey, obese individuals with NASH treated with N-acetylcysteine for 4-12 weeks exhibited an improvement in aminotransferase levels and gamma-GT even though there was no reported change in subject body mass index (Pamuk et al., J Gastroenterol Hepatol 2003; 18(10): 1220-1).

Cysteamine ($HS-CH_2-CH_2-NH_2$) is able to cross cell membranes easily due to its small size. At present, cysteamine is FDA-approved only for the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Treatment with cysteamine has been shown to result in lowering of intracellular cystine levels in circulating leukocytes (Dohil et al., J. Pediatr 2006; 148(6):764-9).

Studies in mice and humans showed cysteamine to be effective in preventing acetaminophen-induced hepatocellular injury (Prescott et al., Lancet 1972; 2(7778):652; Prescott et al., Br Med J 1978; 1(6116):856-7; Mitchell et al., Clin Pharmacol Ther 1974; 16(4):676-84). Cystamine and cysteine have been reported to reduce liver cell necrosis induced by several hepatotoxins. (Toxicol Appl Pharmacol. 1979 April; 48(2):221-8). Cystamine has been shown to ameliorate liver fibrosis induced by carbon tetrachloride via inhibition of tissue transglutaminase (Qiu et al., World J Gastroenterol. 13:4328-32, 2007).

The prevalence of NAFLD in children is unknown because of the requirement of histologic analysis of liver in order to confirm the diagnosis (Schwimmer et al., Pediatrics 2006; 118(4):1388-93). However, estimates of prevalence can be inferred from pediatric obesity data using hepatic ultra-sonongraphy and elevated serum transaminase levels and the knowledge that 85% of children with NAFLD are obese. Data from the National Health and Nutrition Examination Survey has revealed a threefold rise in the prevalence of childhood and adolescent obesity over the past 35 years; data from 2000 suggests that 14-16% children between 6-19 yrs age are obese with a BMI >95% (Fishbein et al., J Pediatr Gastroenterol Nutr 2003; 36(1):54-61), and also that fact that 85% of children with NAFLD are obese.

In patients with histologically proven NAFLD, serum hepatic aminotransferases, specifically alanine aminotransferase (ALT), levels are elevated from the upper limit of normal to 10 times this level (Schwimmer et al., J Pediatr 2003; 143(4):500-5; Rashid et al., J Pediatr Gastroenterol Nutr 2000; 30(1):48-53). The ratio of ALT/AST (aspartate aminotransferase) is >1 (range 1.5-1.7) which differs from alcoholic steatohepatitis where the ratio is generally <1. Other abnormal serologic tests that may be abnormally elevated in NASH include gamma-glutamyltransferase (gamma-GT) and fasting levels of plasma insulin, cholesterol and triglyceride.

The exact mechanism by which NAFLD develops into NASH remains unclear. Because insulin resistance is associated with both NAFLD and NASH, it is postulated that other additional factors are also required for NASH to arise. This is referred to as the "two-hit" hypothesis (Day C P. Best Pract Res Clin Gastroenterol 2002; 16(5):663-78) and involves, firstly, an accumulation of fat within the liver and, secondly, the presence of large amounts of free radicals with increased oxidative stress. Macrovesicular steatosis represents hepatic accumulation of triglycerides, and this in turn is due to an imbalance between the delivery and utilization of free fatty acids to the liver. During periods of increased calorie intake, triglyceride will accumulate and act as a reserve energy source. When dietary calories are insufficient, stored triglycerides (in adipose) undergo lipolysis and fatty acids are released into the circulation and are taken up by the liver. Oxidation of fatty acids will yield energy for utilization. Treatment of NASH currently revolves around the reduction of the two main pathogenetic factors, namely, fat accumulation within the liver and excessive accumulation of free radicals causing oxidative stress. Fat accumulation is diminished by reducing fat intake as well as increasing caloric expenditure. One therapeutic approach is sustained and steady weight loss. Although not definitively proven, a >10% loss in body weight has been shown in some cases to reduce hepatic fat accumulation, normalize liver transaminases and improve hepatic inflammation and fibrosis (Ueno et al., J Hepatol 1997; 27(1):103-7; Vajro et al., J Pediatr 1994; 125(2):239-41; Franzese et al., Dig Dis Sci 1997; 42(7):1428-32).

Reduction of oxidative stress through treatment with anti-oxidants has also been shown to be effective in some studies. For example, obese children who had steatosis were treated with vitamin E (400-1000 IU/day) for 4-10 months (Lavine J Pediatr 2000; 136(6):734-8). Despite any significant change in BMI, the mean ALT levels decreased from 175±106 IU/L to 40±26 IU/L (P<0.01) and mean AST levels decreased from 104±61 IU/L to 33±11 IU/L (P<0.002). Hepatic transaminases increased in those patients who elected to discontinue vitamin E therapy. An adult study using vitamin E for one year demonstrated similar reduction of hepatic transaminases as well as the fibrosis marker TGFβ levels (Hasegawa et al., Aliment Pharmacol Ther 2001; 15(10):1667-72).

Steatosis also may develop into steatohepatitis through oxidative stress due to reactive oxygen species (ROS) and decreased anti-oxidant defense (Sanyal et al., Gastroenterology 2001; 120(5):1183-92). ROS can be generated in the liver through several pathways including mitochondria, peroxisomes, cytochrome P450, NADPH oxidase and lipooxygenase (Sanyal et al., Nat Clin Pract Gastroenterol Hepatol 2005; 2(1):46-53). Insulin resistance and hyperinsulinism has been shown to increase hepatic oxidative stress and lipid peroxidation through increased hepatic CYP2EI activity (Robertson et al., Am J Physiol Gastrointest Liver Physiol 2001; 281(5):G1135-9; Leclercq et al., J Clin Invest 2000; 105(8):1067-75).

Currently, much of what is understood of the pathogenesis of NAFLD has arisen from animal studies. A number of mouse models which exhibit steatosis/steatohepatitis exist and include genetically altered leptin-deficient (ob/ob) or leptin resistant (db/db) and the dietary methionine/choline deficient (MCD) model. Studies comparing male and female rats of varying strains (Wistar, Sprague-Dawley, Long-Evans) with a mouse strain (C57BL/6) as models for NASH have been undertaken. These animals were fed for 4 weeks with an MCD diet; although ALT elevation and steatosis were more noticeable in the Wistar rat, the overall histologic changes in the liver of the mice were more constant with changes due to NASH. More recently the use of supra-nutritional diets in animals has resulted in a NAFLD model that physiologically more resembles the human phenotype. The medical conditions most commonly associated with NAFLD are obesity, Type II diabetes and dyslipidemia. These conditions can be induced by feeding mice and rats with high fat or sucrose diets. Rats fed with a >70% fat-rich diet for 3 weeks developed pan-lobular steatosis, patchy inflammation, enhanced oxidative stress, and increased plasma insulin concentrations suggesting insulin resistance. NASH mice have been induced through intragastric overfeeding. Mice were fed up to 85% in excess of their standard intake for 9 weeks. The mice became obese with 71% increase in final body weight; they demonstrated increase white adipose tissue, hyperglycemia, hyperinsulinemia, hyperleptinemia, glucose intolerance and insulin resistance. Of these mice 46% developed increased ALT (121=/−27 vs 13+/−1 U/L) as well as histologic features suggestive of NASH. The livers of the overfed mice were about twice as large expected, beige in color with microscopic evidence of lipid droplets, cytoplasmic vacuoles and clusters of inflammation.

Mouse models of NASH are created through specific diets (methionine choline deficient, MCD) or intragastric overfeeding. These mice develop serologic and histologic features of NASH. NASH mice are useful in screening and measuring the effects cysteamine on NASH related disease and disorders. For example, the effect of treatment can be measured by separating the NASH mice into a control group where animals will continue to receive MCD diet only and three other treatment groups where mice will receive MCD diet as well as anti-oxidant therapy. The three therapy groups will receive cysteamine 50 mg/kg/day, 100 mg/kg/day and sAME.

Cysteamine is a small molecule (HS—CH2-CH2-NH2) which is able to cross cell membranes easily. Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia.

In addition, sulfhydryl (SH) compounds such as cysteamine, cystamine, and glutathione are among the most important and active intracellular antioxidants. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have appeared demonstrating a protective effect of cysteamine against the hepatotoxic agents acetaminophen, bromobenzene, and phalloidine.

Cystamine, in addition, to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein (Nature Medicine 8, 143-149, 2002). In addition, cystamine was found to increase the levels of certain neuroprotective proteins. However, due to the current methods and formulation of delivery of cystamine, degradation and poor uptake require excessive dosing.

At present, cysteamine is FDA approved only for the treatment of cystinosis. Patients with cystinosis are normally required to take cysteamine every 6 hours. Ideally, an effective controlled-release preparation of cysteamine with perhaps twice daily administration would improve the quality of life for these patients.

The disclosure is not limited with respect to a specific cysteamine or cystamine salt or ester or derivative; the compositions of the disclosure can contain any cysteamine or cystamine, cysteamine or cystamine derivative, or combination of cysteamine or cystamines. The active agents in the composition, i.e., cysteamine or cystamine, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

The methods of compositions of the disclosure further provide enteric-coated compositions that result in less frequent dosing (2×/day vs. 4×/day), increased patient compliance and fewer gastrointestinal side effects (e.g., pain, heartburn, acid production, vomiting) and other side effects (e.g., patients smell like rotten eggs—a particular compliance problem as subjects reach puberty). The disclosure provides enteric-coated cysteamine compositions (sulfhydryl/CYSTAGON®) and cystamine compositions.

The disclosure provides methods for the treatment of fatty acid liver disease, including, but not limited to non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

The effectiveness of a method or composition of the described herein can be assessed, for example, by measuring leukocyte cystine concentrations. Additional measures of the efficacy of the methods of the disclosure include assessing relief of symptoms associated with fatty liver disease including, but not limited to, liver fibrosis, fat content of liver, incidence of or progression of cirrhosis, incidence of hepatocellular carcinoma, elevated hepatic aminotransferase levels, increased alanine aminotransferase (ALT), increased aspartate aminotransferase (AST), and elevated serum ferritin. Dosage adjustment and therapy can be made by a medical specialist depending upon, for example, the severity of fatty liver disease and/or the concentration of cystine. For example, treatment of fatty liver disease may result in a reduction in hepatic transaminase of between approximately 10% to 40% compared to levels before treatment. In a related embodiment, treatment results in a reduction in alanine anminotransferase levels in a treated patient to approximately 30%, 20% or 10% above normal ALT levels, or at normal ALT levels ($\geqq$40 iu/L). In another embodiment, treatment with cysteamine product results in a reduction in aspartate anminotransferase levels in a patient to approximately 30%, 20% or 10% above normal AST levels or back to normal AST levels.

In one embodiment, the disclosure provides methods of treating NAFL using cysteamine products through reducing the oxidative stress caused by reactive oxygen species (ROS) in steatohepatitis. Cysteamine can achieve this through its direct or indirect ability to enhance glutathione levels within the liver. Glutathione has a protective effect against oxidative damage but itself does not enter easily into cells, even when given in large amounts treatment. Precursors of glutathione do, however, enter into cells and include cysteine, N-acetylcyteine, s-adenosylmethionine (SAMe) and other sulphur-containing compounds such as cysteamine.

The compositions of the disclosure can be used in combination with a second agent or other therapies useful for treating NAFLD or NASH or other fatty acid liver disorders. For example, cysteamine product compositions may be administered with drugs such as glitazones/thiazolidinediones that combat insulin resistance, including mesylate (troglitazone (REZULIN®)), rosiglitazone (AVANDIA®), pioglitazone (ACTOS®), as well as other agents, including, but not limited to, metformin, Sulfonylureas, Alpha-glucosidase inhibitors, Meglitinides, vitamin E, tetrahydrolipstatin (XENICAL™), milk thistle protein (SILIPHOS®), and anti-virals.

Other therapies which reduce side effects of cysteamine products can be combined with the methods and compositions of the disclosure to treat diseases and disorders that are attributed or result from NAFLD or NASH. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tablets). Insulin treatment is sometimes necessary if diabetes appears, when the pancreas does not produce enough insulin. These treatments have become rarely necessary in children whom are treated with cysteamine product, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the cysteamine product compositions and methods of the disclosure. Additional therapies including the use of omeprazole (PRILOSEC®) can reduce adverse symptoms affecting the digestive tract.

The disclosure provides cysteamine products useful in the treatment of fatty liver diseases and disorders. To administer cysteamine products of the disclosure to human or test animals, it is preferable to formulate the cysteamine products in a composition comprising one or more pharmaceutically acceptable carriers. As set out above, pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The cysteamine product compositions may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Pharmaceutical compositions of the disclosure containing a cysteamine product as an active ingredient may contain pharmaceutically acceptable carriers or additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline®, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the disclosure.

Formulation of the pharmaceutical composition will vary according to the route of administration selected (e.g., solution, emulsion). An appropriate composition comprising the cysteamine product to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, the cysteamine product of this disclosure can be lyophilized for storage and reconstituted in a suitable carrier prior to use. Any suitable lyophilization and reconstitution techniques can be employed. It is appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the disclosure provides use of an enterically coated cysteamine product composition. Enteric coatings prolong release until the cysteamine product reaches the intestinal tract, typically the small intestine. Because of the enteric coatings, delivery to the small intestine is improved thereby improving uptake of the active ingredient while reducing gastric side effects.

In some embodiments, the coating material is selected such that the therapeutically active agent is released when the dosage form reaches the small intestine or a region in which the pH is greater than pH 4.5. The coating may be a pH-sensitive material, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5. For example, pH-sensitive materials will not undergo significant dissolution until the dosage from has emptied from the stomach. The pH of the small intestine gradually increases from about 4.5 to about 6.5 in the duodenal bulb to about 7.2 in the distal portions of the small intestine. In order to provide predictable dissolution corresponding to the small intestine transit time of about 3 hours (e.g., 2-3 hours) and permit reproducible release therein, the coating should begin to dissolve at the pH range within the small intestine. Therefore, the amount of enteric polymer coating should be sufficient to substantially dissolved during the approximate three hour transit time within the small intestine, such as the proximal and mid-intestine.

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit®L30D) (F. W. Goodhart et al. Pharm. Tech., pp. 64-71, April 1984); copolymers of methacrylic acid and methacrylic acid methylester (Eudragit®), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See, Rernington's at page 1590, and Zeitova et al., (U.S. Pat. No. 4,432,966), for descriptions of suitable enteric coating compositions. Accordingly, increased adsorption in the small intestine due to enteric coatings of cysteamine product compositions can result in improved efficacy.

Generally, the enteric coating comprises a polymeric material that prevents cysteamine product release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a pKa in the range of about 3 to 5. Suitable enteric coating materials include, but are not limited to, polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit® NE, Eudragit® RL, Eudragit® RS). For example, the enterically coating can comprise Eudragit® L30D, triethylcitrate, and hydroxypropylmethylcellulose (HPMC), wherein the coating comprises 10 to 13% of the final product.

In one embodiment, the cysteamine product composition is administered in tablet form. Tablets are manufactured by first enterically coating the cysteamine product. A method for forming tablets herein is by direct compression of the powders containing the enterically coated cysteamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In some embodiments, the cysteamine product composition is a delayed or controlled release dosage form that provides a $C_{max}$ of the cysteamine product that is at least about 35%, 40%, 45%, 50%, 55%, 60%, 65%, 70%, 75%, 80%, 85%, or 100% higher than the $C_{max}$ provided by an immediate release dosage form containing the same amount of the cysteamine product. In some embodiments, the $C_{max}$ is up to about 75%, 100%, 125% or 150% higher than the $C_{max}$ of the immediate release dosage form. $C_{max}$ refers to the maximum dose of the cysteamine product in the blood after dosing and provides an indicator that the drug is absorbed systemically.

In some embodiments, the AUC of the delayed or controlled release dosage form is also increased by at least about 20%, 25%, 30%, 35%, 40%, 45%, or 50%, or up to about 50%, 60%, 75% or 100% relative to an immediate release dosage form. AUC or "area under the curve", and refers to the kinetic curve derived when plasma drug concentration versus time is measured after dosing of a drug.

The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an in soluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For further detail, see the Handbook of Pharmaceutical Controlled Release Technology, Wise, ed., Marcel Dekker, Inc., New York, N.Y. (2000), incorporated by reference herein in its entirety, e.g. Chapter 22 ("An Overview of Controlled Release Systems").

The concentration of cysteamine product in these formulations can vary widely, for example from less than about 0.5%, usually at or at least about 1% to as much as 15 or 20% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

The cysteamine product is present in the composition in a therapeutically effective amount; typically, the composition is in unit dosage form. The amount of cysteamine product administered will, of course, be dependent on the age, weight, and general condition of the subject, the severity of the condition being treated, and the judgment of the prescribing—physician. Suitable therapeutic amounts will be known to those skilled in the art and/or are described in the pertinent reference texts and literature. Current non-enterically coated doses are about 1.35 g/m$^2$ body surface area and are administered 4-5 times per day. In one aspect, the dose is administered either one time per day or multiple times per day. The cysteamine product may be administered one, two or three or four or five times per day. In some embodiments, an effective dosage of cysteamine product may be within the range of 0.01 mg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. In some embodiments, the cysteamine product is administered at a total daily dose of from approximately 0.25 g/m$^2$ to 4.0 g/m$^2$ body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m$^2$. In some embodiments, the cysteamine product may be administered at a total daily dose of about 1-1.5 g/m$^2$ body surface area, or 0.5-1 g/m$^2$ body surface area, or about 0.7-0.8 g/m$^2$ body surface area, or about 1.35 g/m$^2$ body surface area. Salts or esters of the same active ingredient may vary in molecular weight depending on the type and weight of the salt or ester moiety. For administration of the dosage form, e.g., a tablet or capsule or other oral dosage form comprising the enterically coated cysteamine product, a total weight in the range of approximately 100 mg to 1000 mg is used. The dosage form is orally administered to a patient suffering from fatty liver disease for which an cysteamine product would be indicated, including, but not limited to, NAFLD and NASH. Administration may continue for at least 3 months, 6 months, 9 months, 1 year, 2 years, or more.

Compositions useful for administration may be formulated with uptake or absorption enhancers to increase their efficacy. Such enhancer include for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

The enterically coated cysteamine product can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the cysteamine product. For solid compositions, diluents are typically necessary to increase the bulk of a tablet so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum. Lubricants are used to facilitate tablet manufacture; examples of suitable lubricants include, for example, magnesium stearate, calcium stearate, and stearic acid, and are typically present at no more than approximately 1 weight percent relative to tablet weight. Disintegrants are used to facilitate tablet disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of cysteamine product to the stabilizing agent is at least about 1:500 w/w, more commonly about 1:99 w/w.

The tablets can be manufactured by first enterically coating the cysteamine product. A method for forming tablets herein is by direct compression of the powders containing the enterically coated cysteamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In an alternative embodiment, the enterically coated cysteamine product are granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein.

For administration of the dosage form, i.e., the tablet or capsule comprising the enterically coated cysteamine product, a total weight in the range of approximately 100 mg to 1000 mg is used. The dosage form is orally administered to a patient suffering from a condition for which an cysteamine product would typically be indicated, including, but not limited to, NAFLD and NASH.

The compositions of the disclosure can be used in combination with other therapies useful for treating NAFL and NASH. For example, antioxidants such as glycyrrhizin, schisandra extract, ascorbic acid, glutathione, silymarin, lipoic acid, and d-alpha-tocopherol, and parenterally administering to the subject glycyrrhizin, ascorbic acid, glutathione, and vitamin B-complex may be administered in combination (either simultaneously in a single composition or in separate compositions). Alternatively, the combination of therapeutics can be administered sequentially.

The effectiveness of a method or composition of the disclosure can be assessed by measuring fatty acid content and metabolism in the liver. Dosage adjustment and therapy can be made by a medical specialist depending upon, for example, the severity of NAFL.

In addition, various prodrugs can be "activated" by use of the enterically coated cysteamine. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of produgs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated cysteamine compositions of the disclosure (at a desired time) to activate the pro-drug.

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

EXAMPLES

Example 1

Formulation of Enteric Coated Cysteamine. International Publication No. WO 2007/089670 described administration of cysteamine to cystinosis patients using a nasoenteric tube to determine the efficacy of enteric administration on the improvement in cystinosis patients. WO 2007/089670 showed that administration of cysteamine enterically improved the absorption rate of cysteamine and increased plasma cysteamine levels. Enteric administration also reduced the levels of cystine in leukocytes. These results showed that enteric cysteamine was more efficacious than oral administration of cysteamine.

An enteric coated preparation on cysteamine (Cystagon-EC) was created for more efficacious and easier administration. CYSTAGON® capsules (Myian Laboratories Inc., PA, USA) were enterically coated using a Model 600 Wurster coating unit with a ⅘" coating chamber. Coating material is Eudragit® L30 D-55, Rohm GmbH & Co KG, Darmstadt, Germany) and the EC compound was encapsulated (The Coating Place Inc, Verona, Wis., Federal facilities establishment number 2126906). Capsules were produced using FDA approved facilities and materials.

Enteric coating was tested in vitro to verify the insolubility of the capsules in gastric acid. Testing was done by placing the capsules into 100 mL 0.1N HCL solution for 2 hours at 37° C. Capsules are considered acceptable if less than 10% of the cysteamine is released. After 2 hours the pH of the solution is raised to pH 6.8 with $NaHCO_3$ buffer. Capsules are considered acceptable if at least 80% of the cysteamine is released within 2 hours.

Six adult controls subjects and 6 patients with cystinosis have been studied using the Cystagon-EC. The plasma cysteamine levels were higher when the patient took Cystagon-EC than when they took the regular cysteamine (CYSTAGON®) preparation. In addition, when cystinosis patients took Cystagon-EC the 12 hour trough white cell cystine levels remained at about <0.2 and usually below 1 nmol of half-cystine/mg protein, suggesting that this new formulation of cysteamine is effective when given twice daily.

Example 2

Administration of Cysteamine to Patients Suffering From Fatty Liver Disease. Administration of cysteamine has been shown to relieve symptoms of cystinosis by decreasing levels of damaging cystine. To determine the effect of cysteamine on the fibrosis that causes liver damage in NASH patients, an open-label, non-randomized, pilot study of 12 children and adolescents with non-alcoholic fatty disease treated with enteric-coated cysteamine is performed.

Patients with an established diagnosis of NASH, who have undertaken lifestyle changes (such as diet and exercise) for at least three months, are used for the study. A full history and physical examination is taken. A symptom score devised for acid-peptic disease and previously used in children taking cysteamine is used. Blood is drawn for liver functions including hepatic transaminases, alkaline phosphatase, bilirubin and gamma-GT. Blood is also taken for complete blood count, ESR, CRP, fasting insulin and fasting lipid and cholesterol profile, markers of oxidative stress and of liver fibrosis (total 15 ml). Patients weight is recorded.

The study entry level for ALT is defined as $\geq 60$ iu/L and a successful response to therapy is normalization or >35% reduction in hepatic transaminase level. A normal ALT level is defined as 40 iu/L. Subjects are started on enteric-coated cysteamine twice daily at a total daily dose of 1 g/m² body surface area with a maximum dose of 1000 mg twice daily. Patients with cystinosis normally take 1-1.5 g/m² body surface area/day.

Any subject complaining of significant gastrointestinal symptoms may have his/her dose daily dose of cysteamine reduced by 10%. If GI symptoms persist for 3 days despite a 10% decrease in dosage, then further 10% decrements in dosage will permitted (to a maximum of 50% of the original dose). If symptoms persist despite the maximum decrease in EC-cysteamine dose, the subject is removed from the study.

If symptoms are severe, subjects may exit the study at any point. If patients were on acid-suppression therapy such as proton-pump inhibitors, they are asked to discontinue therapy one week before commencing EC-cysteamine. Patients are treated initially for 3 months, and for a maximum of 6 months, with EC-cysteamine. If a 10-25% reduction in hepatic transaminase levels are detected then treatment is extended for a further 3 months. If, however, there is <10% reduction of ALT level after 3 months therapy, the subject will take no further part in the study. If there is an improvement in serum hepatic transaminase levels (>35%) after six months of therapy, then patients are monitored for a further six months with a physical examination and the same blood tests performed every two months. Menstruating females will undergo a blood pregnancy test at the start and every month during the study. If appropriate, patients are advised to take contraceptive precautions using double barrier method.

Patients are asked to maintain a diary of symptoms and will also be seen in the GCRC/clinic in order to obtain information with about are blinded to the identity of the patient's study drug. A symptom score devised for acid-peptic disease and previously used in children taking cysteamine is used. Every 4 weeks patients will have repeat blood tests including liver function tests, complete blood count, and plasma cysteamine levels (10 ml). At the end of the study, patients will have all baseline laboratory tests repeated.

Example 3

The effect of a cysteamine product was evaluated in a dietary animal model of non-alcoholic fatty liver disease (NAFLD), carried out generally as described in Otogawa et al., Am. J. Pathol., 170(3):967-980 (2007). Male New Zealand white rabbits were fed a high-fat diet (HFD) containing 20% corn oil and 1.25% cholesterol in order to induce clinical and histological features characteristic of NAFLD and non-alcoholic steatohepatitis (NASH). A pilot study of 7-days duration was carried out using intraperitoneal (IP) dosing of cysteamine bitartrate on an every 8 hour schedule (Q8H) at two dose levels: 75 or 250 mg/kg/day. A longer study of 8-weeks duration delivered cysteamine bitartrate in the drinking water at 25, 75 or 250 mg/kg/day.

As discussed in further detail below, the data from both studies showed that cysteamine treatment produced an improvement in levels of hepatic transaminase (aspartate aminotransferase, or AST) compared to the HFD untreated control group. AST elevation is considered one of the best markers of liver inflammation in NAFLD and NASH. Compared to the HFD diet control animals, AST levels were reduced by 1.6- to 1.9-fold with cysteamine treatment, i.e., reductions of 37 to 47%, respectively. The data also showed that cysteamine treatment was associated with beneficial changes in LDH, a general marker of tissue damage, and beneficial changes in lipid profile markers such as total cholesterol, LDL-cholesterol, and HDL-cholesterol, compared to the HFD control groups. The improvements observed in these rabbit models support the conclusion that cysteamine treatment of human non-alcoholic fatty liver diseases (NAFLD) including NASH may confer clinical benefits.

Pilot Study. In the pilot study, two different dose levels of cysteamine were delivered by the intraperitoneal (IP) route every 8 hours (Q8H) for 7 days to New Zealand white rabbits fed a high-fat diet (HFD). Male rabbits between 2.5 to 3.5 kg were divided into the following groups: 1) control standard diet, 2 animals, 2) control HFD, 2 animals, 3) low dose cysteamine bitartrate, 75 mg/kg/day, HFD, 4 animals, and 4) high dose cysteamine bitartrate, 250 mg/kg/day, HFD, 4 animals. Endpoints included daily standard clinical observations, quantitative daily food consumption, body weights on Study Day (SD) −1, 2, 5, and 8 (day of necropsy), and blood samples collected on SD-1 and SD8 for the evaluation of selected clinical chemistries (alanine aminotransferase (ALT), aspartate aminotransferase (AST), amylase, lipase, total cholesterol, triglycerides, lactate dehydrogenase (LDH), high density lipoprotein cholesterol (HDL-cholesterol), and low density lipoprotein cholesterol (LDL-cholesterol)) and a full hematology panel. Animals were sacrificed on SD8.

No pharmacologically important differences were found regarding the clinical observations, the body weights, or hematology values obtained at baseline on SD-1 and SD8. The values observed for ALT, amylase, lipase, triglycerides, and HDL-cholesterol were not different between the groups over the 7 days of the study. However, increases were observed in total cholesterol, LDL-cholesterol and LDH values in those animals fed the HFD.

Importantly, compared to the HFD control group, the groups treated with cysteamine showed improvements in four serum chemistry values: AST, total cholesterol, LDL-cholesterol, and LDH.

AST has emerged as the best marker of liver inflammation in NASH and is considered to be a superior marker to ALT. Compared to the HFD control group, a decrease was observed in the mean AST values on SD8 in the high dose cysteamine group (250 mg/kg/day), as shown in FIG. 1. The mean AST value for the control HFD group was 19.0 U/L, whereas the rabbits that received 250 mg/kg/day cysteamine showed a 1.9-fold decrease in this value to 10.0 U/L, or only 47% of the control HFD value. Because there were only 2 animals in the control HFD group, it was not possible to make statistical comparisons. However, comparison of the AST results of the 75 mg/kg/day group on SD8 against those of the 250 mg/kg/day cysteamine animals indicated that the high dose cysteamine group was statistically different from the low dose group by the Mann-Whitney U test, p=0.03. These data showed that cysteamine treatment at 250 mg/kg/day on this regimen had a positive impact on AST values.

Figure 2:
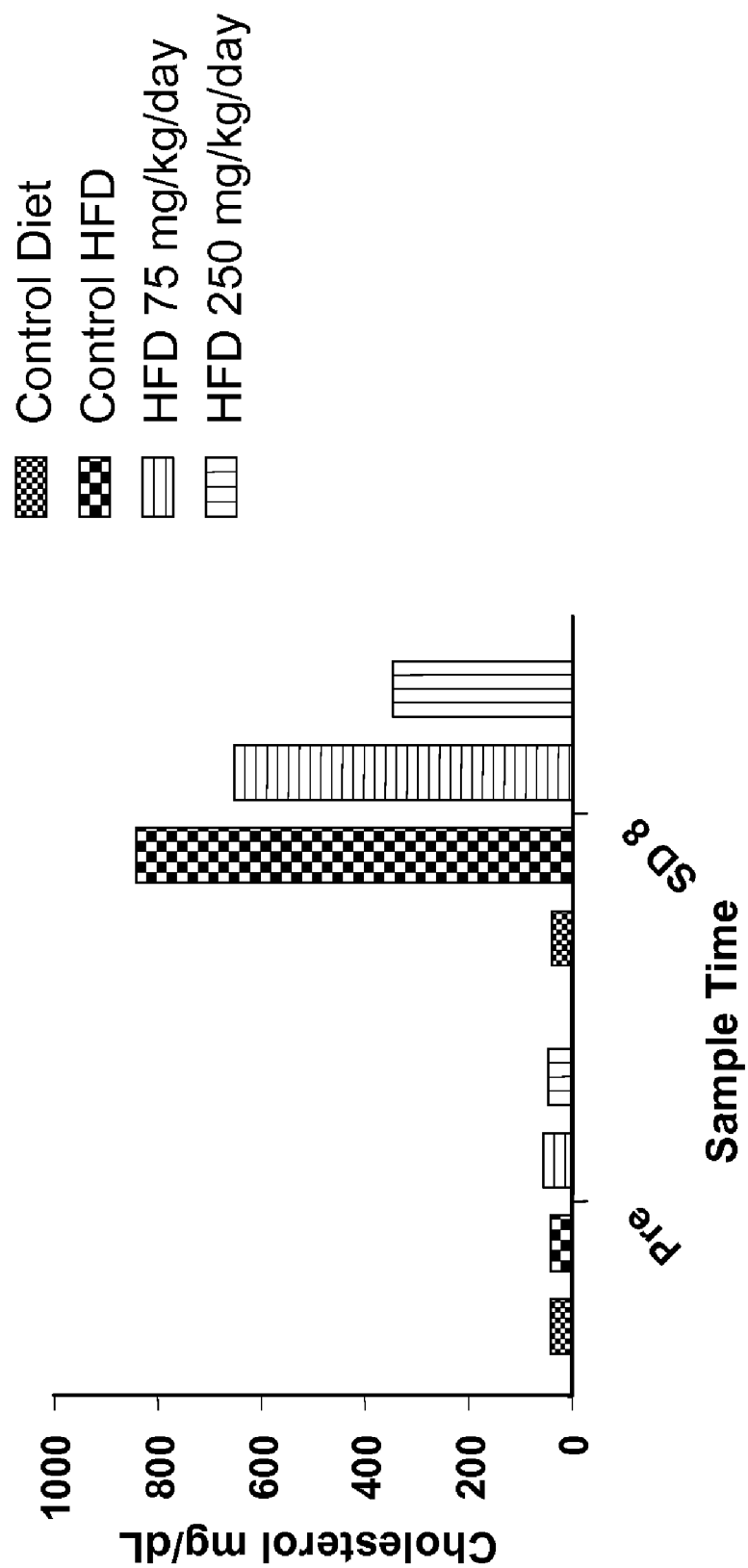
FIG. 2 shows the effect of cysteamine treatment at 0, 75 and 250 mg/kg/day, delivered intraperitoneally, on cholesterol levels in animals fed a HFD for 8 days. Cholesterol levels for control animals, not fed a HFD, are also shown. The graph depicts mean cholesterol values from blood samples collected on study day-1 ("pre") and on study day 8 (SD8).

Mean serum total cholesterol values at baseline (SD-1) ranged from 42.5 to 55.25 mg/dL across all groups, which is within the lab's historical range for normal rabbits of 20-78 mg/dL. On SD8, rabbits who received cysteamine at either 75 or 250 mg/kg/day were found to have less of an increase in mean total cholesterol as compared to the control HFD group, as shown in FIG. 2. The control rabbits in Group 2 on the HFD had a mean total cholesterol value of 842 mg/dL on SD8, approximately a 20-fold increase over their baseline values. The Group 3 rabbits, who received 75 mg/kg/day cysteamine, had a mean value of 652 mg/dL, only about a 12-fold increase over their baseline value, or 23% less of an increase than the HFD controls. The rabbits in Group 4, who received 250 mg/kg/day cysteamine, had a mean value of 347 mg/dL on SD8, only about a 7.5-fold increase over their baseline value, or 59% less of an increase than the HFD control values. These data showed that cysteamine treatment resulted in a clear dose-dependent reduction in the serum total cholesterol increase due to the HFD diet.

Figure 3:
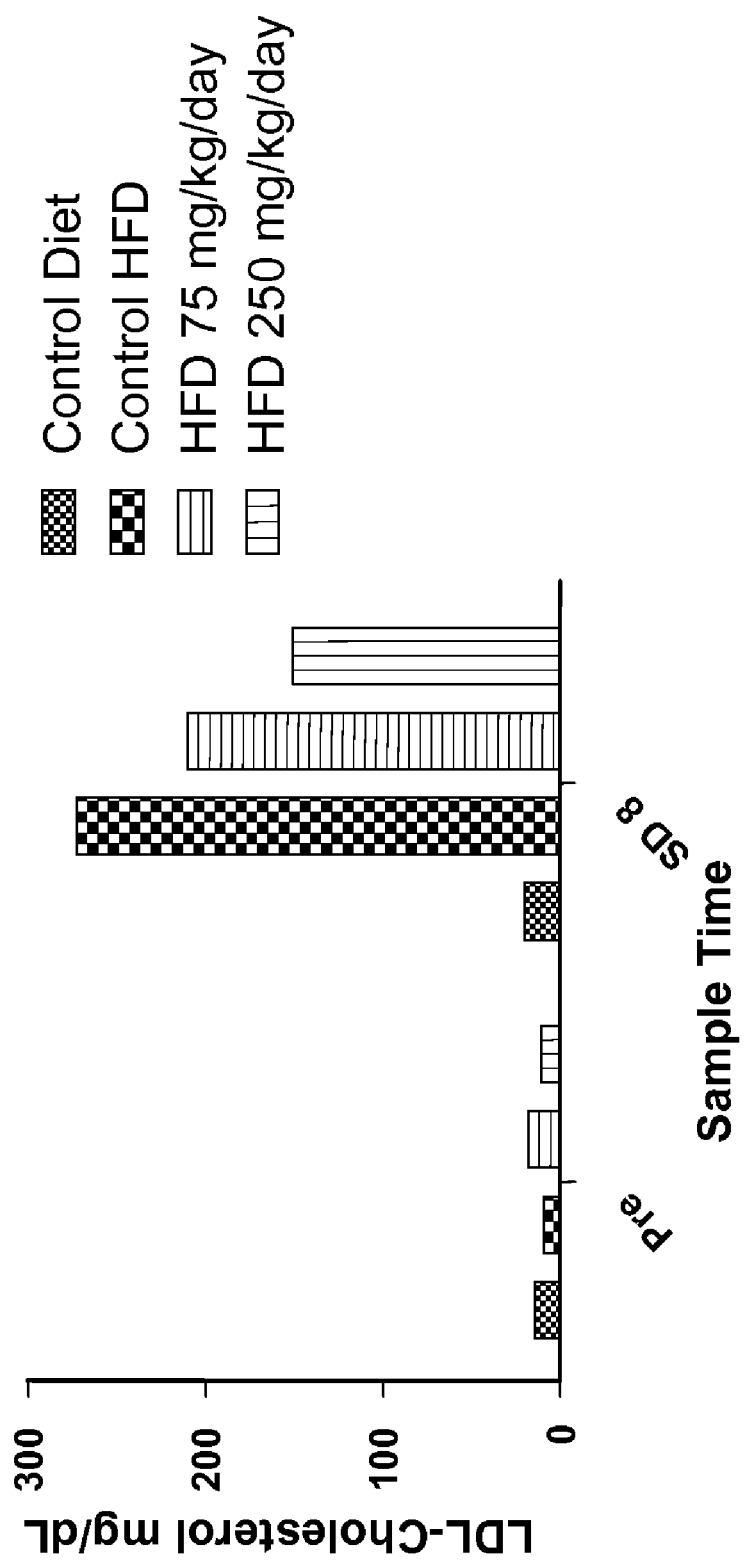
FIG. 3 shows the effect of cysteamine treatment at 0, 75 and 250 mg/kg/day, delivered intraperitoneally, on low density lipoprotein-cholesterol (LDL-cholesterol) levels in animals fed a HFD for 8 days. LDL-cholesterol levels for control animals, not fed a HFD, are also shown. The graph depicts mean LDL-cholesterol values from blood samples collected on study day-1 ("pre") and on study day 8 (SD8).

LDL-cholesterol values also appeared to be impacted by cysteamine dosing. As seen with the total cholesterol marker, the increase in LDL-cholesterol observed in the control HFD group was noticeably lessened in those rabbits treated with cysteamine at either 75 or 250 mg/kg/day, as shown in FIG. 3. The mean LDL-cholesterol value across all groups at baseline ranged from 9.5 to 18 mg/dL, within the lab's historical range of 4 to 19 mg/dL. On SD8, the control HFD rabbits had a mean value of 272.5 mg/dL, an increase of about 29-fold over baseline. The rabbits in Group 3 treated with 75 mg/kg/day cysteamine had a mean value of 210 mg/dL on SD8, an increase of only about 12-fold compared to their respective baseline values, or 23% less of an increase than the HFD controls. The rabbits in Group 4 treated with 250 mg/kg/day had a mean LDL-cholesterol value of 150.5 mg/dL, an increase of only about 14-fold compared to their baseline values, or 45% less of an increase than the HFD controls.

These data showed that cysteamine treatment resulted in notable reductions in the LDL-cholesterol increases due to the HFD diet.

Figure 4:
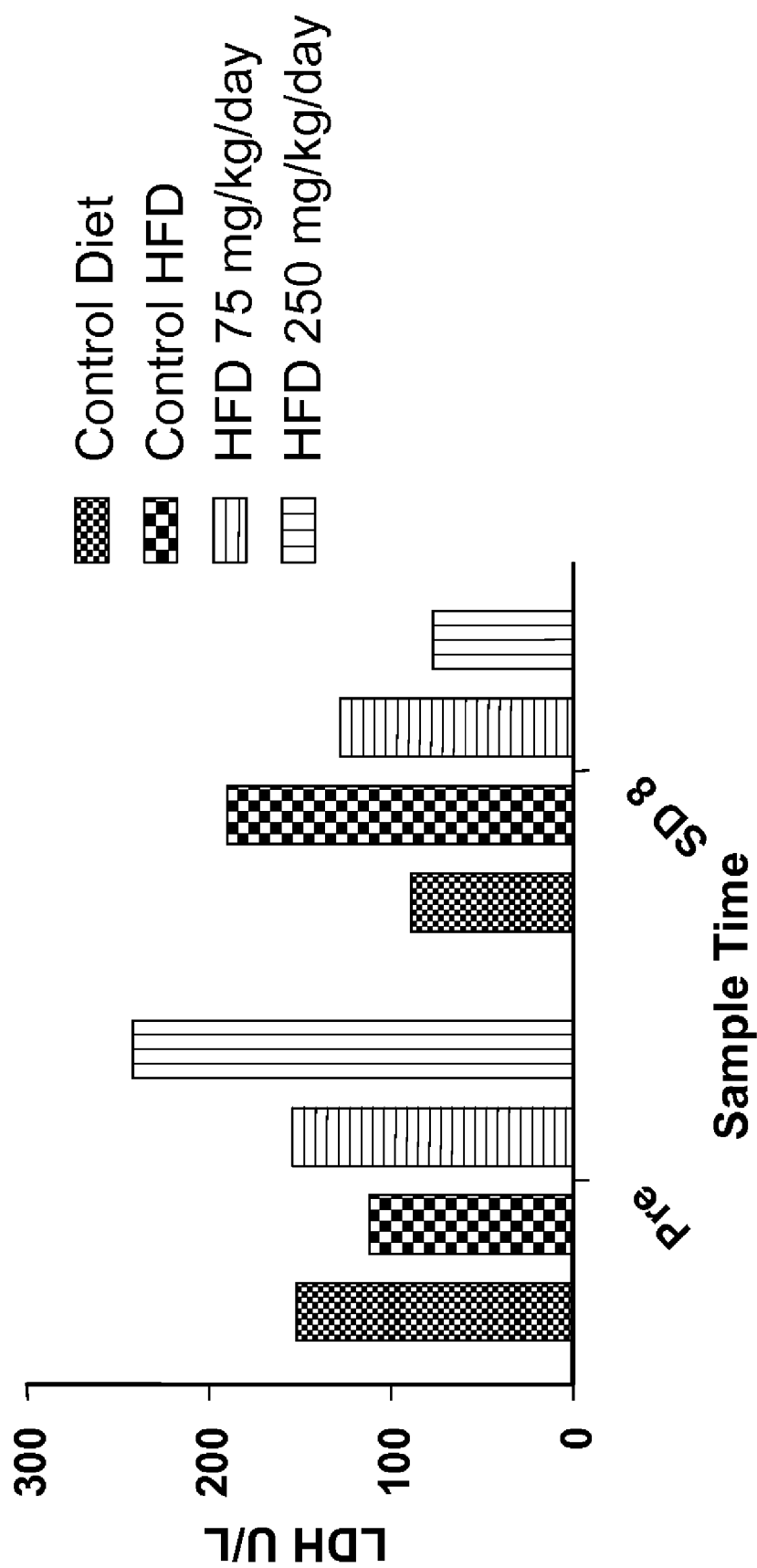
FIG. 4 shows the effect of cysteamine treatment at 0, 75 and 250 mg/kg/day, delivered intraperitoneally, on lactate dehydrogenase (LDH) levels in animals fed a HFD for 8 days. LDH levels for control animals, not fed a HFD, are also shown. The graph depicts mean LDH values from blood samples collected on study day −1 ("pre") and on study day 8 (SD8).

LDH values showed a similar trend: rabbits that received cysteamine at either 75 or 250 mg/kg/day had less of an increase in LDH than the control HFD rabbits, as shown in FIG. 4. The control HFD rabbits in Group 2 had a mean LDH value of 190 U/L on SD8, an increase of 1.7-fold over their baseline values. The rabbits in Group 3 (75 mg/kg/day) had mean values of 128 U/L on SD8, which was a decrease of 1.2-fold compared to their baseline values, or 33% of the control HFD values on SD8. The rabbits in Group 4 (250 mg/kg/day) had mean values of 77.5 U/L on SD8, which was a decrease of 3.1-fold compared to their baseline values, or 59% of the control HFD values on SD8. These data showed that cysteamine treatment resulted in a dose dependent reduction of these LDH values as compared to the control rabbits fed the HFD.

The data show that treatment of rabbits fed a HFD with cysteamine bitartrate at either 75 or 250 mg/kg/day IP on a Q8H schedule resulted in an improvement in levels of liver transaminase (AST), an important marker of liver inflammation and damage in NAFLD. Cysteamine treatment was also associated with beneficial changes in the biochemical serum markers total cholesterol, LDL-cholesterol, and LDH. Taken together, the data support the conclusions that cysteamine treatment may confer clinical benefits in human patients with NAFLD such as NASH.

8-Week Study. The purpose of this study was to evaluate the effects of cysteamine treatment in an animal model of NAFLD and NASH in which male New Zealand white rabbits are fed a high fat diet (HFD) containing 20% corn oil and 1.25% cholesterol to produce clinical and histological features characteristic of NAFLD and NASH.

The study design included five groups of eight rabbits. Two control groups did not receive cysteamine in their drinking water: a control group that was fed conventional rabbit chow, and another control group that was fed the HFD. In three groups of rabbits fed the HFD, cysteamine bitartrate was introduced in the drinking water at concentrations calculated to deliver either 25, 75, or 250 mg/kg/day. Drinking water was prepared fresh daily based on room temperature stability information for cysteamine bitartrate across this concentration range.

Observations during the study included twice weekly body weights, daily food and water consumption, and daily clinical observations. Blood samples were collected prior to the start of the study, and on weeks 2, 4, 6, and 8 for a full panel of hematology parameters and a selected panel of serum chemistries, including ALT, AST, amylase, lipase, total cholesterol, triglycerides, LDH, HDL-cholesterol, and LDL-cholesterol.

In all groups that received the HFD, clinical observations such as rough coats and quiet behavior began to be observed around the middle of week 8, while signs of jaundice began to appear earlier, in the middle of week 6. Some animals displayed dark or red colored urine in these same timeframes, suggesting possible bile blockages (cholestasis). Throughout the study, animals on the HFD much more frequently exhibited soft stools compared to the animals on the standard diet. Animals on the HFD also exhibited histological features suggestive of NAFLD. Three animals in Group 4, the mid-dose cysteamine group, died on study or were sacrificed moribund on SD 51, 55, and 56. One animal in Group 5, the high dose group, was sacrificed moribund on SD 55. These deaths on study appeared to be associated with advanced NAFLD.

The body weight data showed that animals on the standard diet and the HFD gained weight at approximately the same rate during the first 6 weeks of the study. However, beginning by week 7, the animals on the HFD began to lose weight compared to the standard diet. The body weights of the cysteamine treated animals seemed to parallel those of the control HFD animals. The food consumption data showed that the animals fed the HFD consumed less food than those on the standard diet after the first week of the study, which would be expected due to the higher caloric content of the HFD. The food consumption of the treated groups and the HFD control group was similar. By around week 6, animals on the HFD were consuming only about 15 to 30% of the amount of food consumed by animals on the standard diet based on the area under the curve (AUC).

The water consumption data followed a similar pattern. All animals on the HFD consumed less water than those on the standard diet, presumably due to a higher moisture content in the HFD. Based on AUCs, the control HFD group consumed about 65% of the water consumed by the animals on the standard diet. The groups that drank cysteamine-containing water consumed about two-thirds of the water consumed by the HFD control group. These data would suggest that the cysteamine-containing water may have been somewhat less palatable than the control water to these rabbits.

The hematology data did not reveal pharmacologically important changes across the study. There was a trend to slightly increased white blood cell (WBC) counts in the control rabbits fed the HFD compared to the standard diet controls, primarily due to lymphocytes. The cysteamine-treated groups were similar to the HFD control group.

The serum chemistry data reflected differences in the control animals fed the HFD compared to the standard diet control animals. At the end of the study (week 8), the HFD control animals in Group 2 had increases in AST (2.6-fold), lipase (6.6-fold), cholesterol (64-fold), triglyceride (3.8-fold), LDH (3-fold), HDL-cholesterol (2.3-fold), and LDL-cholesterol (55-fold) compared to the standard diet control values (Group 1). Amylase and ALT values were unchanged.

Figure 5:
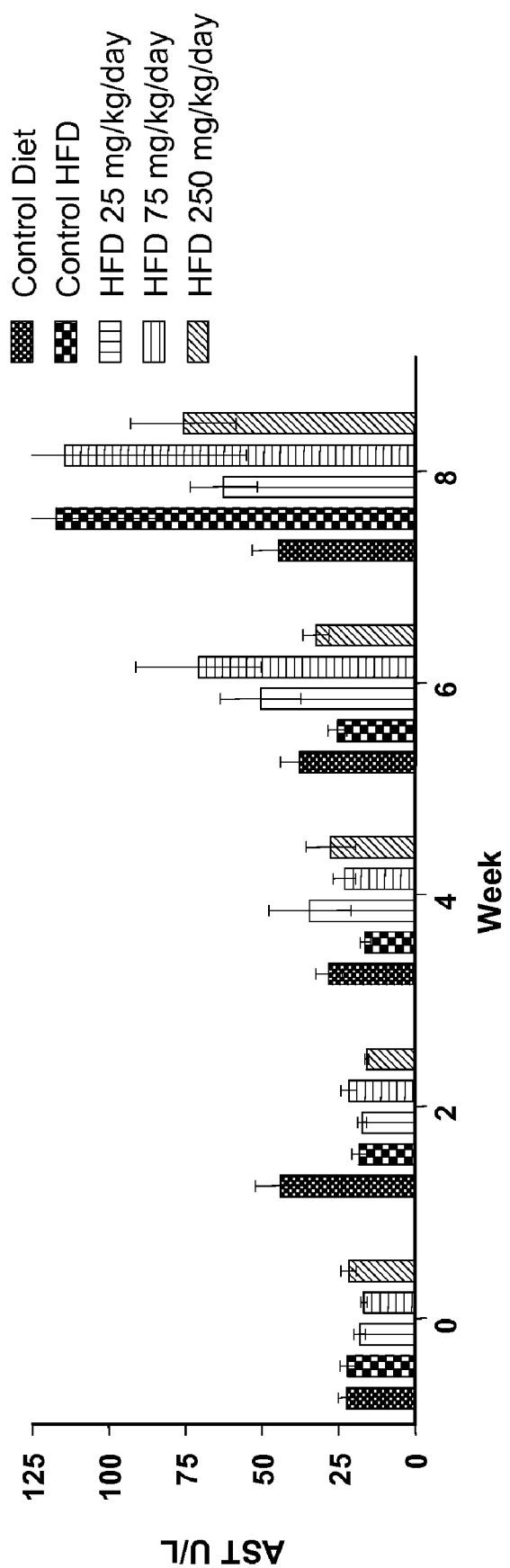
FIG. 5 shows the effect of cysteamine treatment at target doses of 0, 25, 75 and 250 mg/kg/day, delivered via drinking water, on AST levels in animals fed a HFD for 8 weeks. AST levels for control animals, not fed a HFD, are also shown. The graph depicts mean AST values±SEM from blood samples collected on study day-1 ("week 0") and on the last day of the week indicated (week 2, 4, 6 or 8).

AST is considered to be a better marker of hepatic inflammation than ALT. At 8 weeks, control animals fed the HFD had a mean AST value of 117.1 U/L, a 2.6-fold increase compared to control animals fed a standard diet, as shown in FIG. 5. However, the mean AST values in both the low-dose (25 mg/kg/day) and the high-dose (250 mg/kg/day) cysteamine treatment groups were decreased compared to the control HFD animals. The Group 3 animals (25 mg/kg/day) had a mean AST value of only 62.5 U/L, a 1.9-fold decrease relative to the HFD control group, a reduction of 47%. Similarly, the Group 5 animals (250 mg/kg/day) had a mean AST value of only 75.7 U/L, a 1.6-fold decrease relative to HFD controls, a reduction of 35%. Given the difficulties in assessing drug delivery by supplying cysteamine in the drinking water, it is notable that these decreases in AST values were associated with two out of the three cysteamine treatment groups. Similar decreases in AST were also found in the pilot study.

Figure 6:
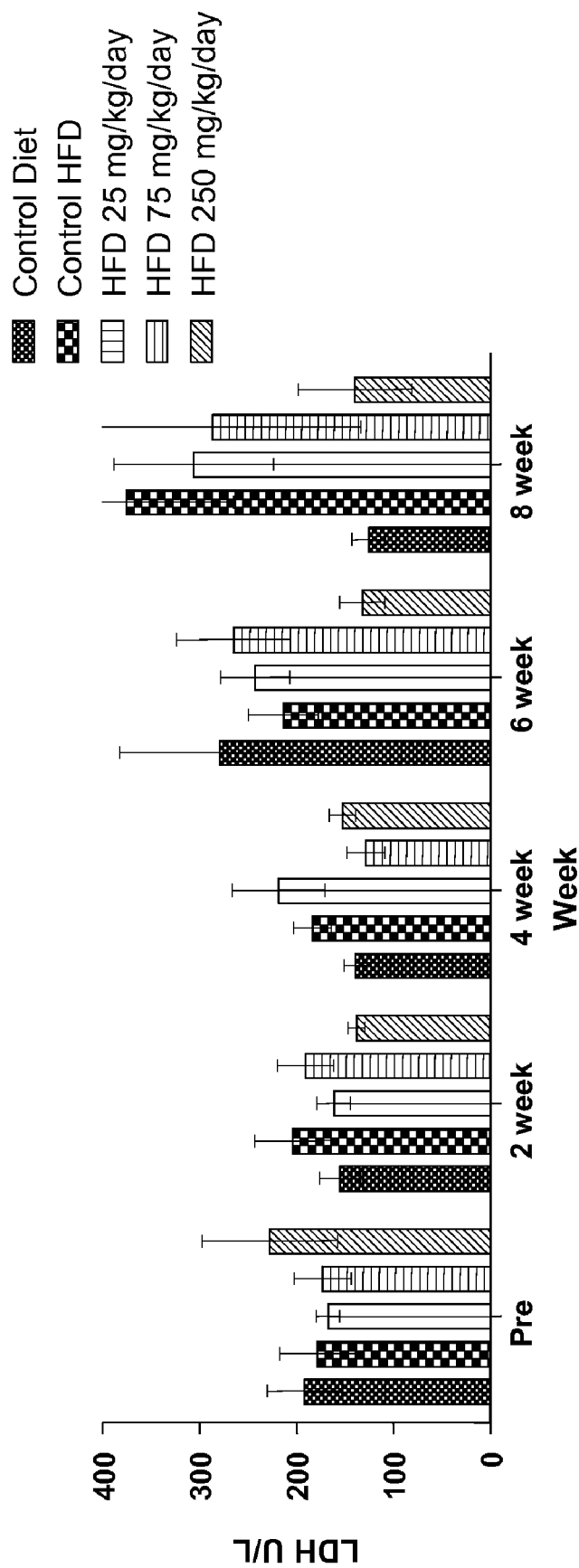
FIG. 6 shows the effect of cysteamine treatment at target doses of 0, 25, 75 and 250 mg/kg/day, delivered via drinking water, on LDH levels in animals fed a HFD for 8 weeks. LDH levels for control animals, not fed a HFD, are also shown. The graph depicts mean LDH values±SEM from blood samples collected on study day-1 ("week 0") and on the last day of the week indicated (week 2, 4, 6 or 8).

As observed in the pilot study, decreases in LDH were also observed in this study in animals treated with cysteamine. As shown in FIG. 6, at week 8 the mean LDH value was 375 U/L in the Group 2 HFD control animals. Exposure to cysteamine resulted in a decrease in LDH values at all three dose levels in the treated animals compared to the Group 2 HFD controls. In Group 5, the high dose (250 mg/kg/day) group, the mean LDH value at week 8 was 140 U/L, nearly identical to the Group 1 standard diet control group mean LDH value of 125.6 U/L. This difference between the HFD control LDH value and the high-dose cysteamine (250 mg/kg/day) value was statistically significant by the Mann-Whitney U test, p=0.03. These data showed that cysteamine treatment markedly reduced the increase in LDH caused by the HFD.

Figure 7:
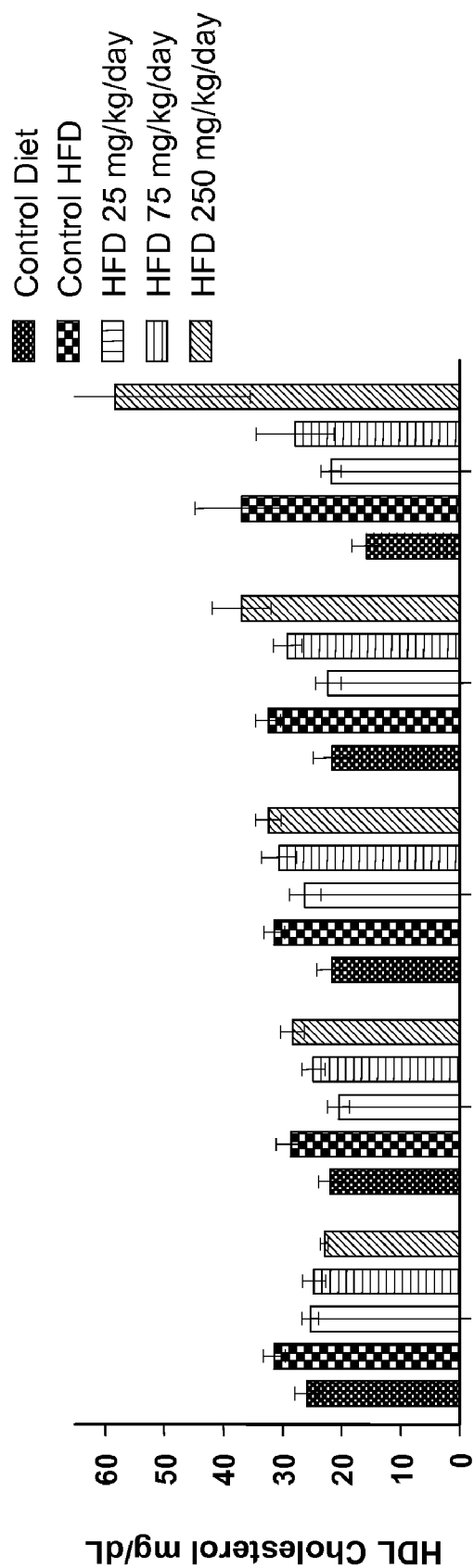
FIG. 7 shows the effect of cysteamine treatment at target doses of 0, 25, 75 and 250 mg/kg/day, delivered via drinking water, on high density lipoprotein cholesterol (HDL-cholesterol) levels in animals fed a HFD for 8 weeks. HDL-cholesterol levels for control animals, not fed a HFD, are also shown. The graph depicts mean HDL-cholesterol values±SEM from blood samples collected on study day-1 ("week 0") and on the last day of the week indicated (week 2, 4, 6 or 8).

It is well-recognized that HDL-cholesterol levels are positive indicators of healthy lipid profiles. Rabbits are known to be a particularly good model for human lipid profiles because they have baseline ratios similar to those found in humans, and they are considered a good model of human cardiovascular disease. Therefore, it was notable that in this study, animals treated with the high-dose cysteamine (250 mg/kg/day) showed a beneficial increase in HDL-cholesterol compared to both the standard diet control group as well as the HFD control group, as shown in FIG. 7. At week 8, the mean HDL-cholesterol value in the 250 mg/kg/day cysteamine group was 58.3 mg/dL, a 1.6-fold increase over the HFD control mean value of 36.9 mg/dL, and a 3.7-fold increase over the control standard diet value of 15.7 mg/dL.

Taken together, the data collected in this 8-week study showed that rabbits fed the HFD developed clinical and serological features associated with liver disease consistent with NAFLD and NASH. Cysteamine dosing in the water bottles likely resulted in variable delivery of the drug to the treated animals. Nonetheless, it was found that two of the same serum chemistry markers that were improved in the pilot study were also improved in this 8-week study in the presence of cysteamine: AST and LDH. These were considered important findings given that AST is considered to be the best marker of inflammation in human NASH and that reductions in LDH probably also reflect less inflammation and likely protection from cytotoxicity in these animals.

Another notable finding in this longer term study was that cysteamine treatment was associated with a beneficial rise in the serum HDL-cholesterol levels.

Numerous modifications and variations in the invention as set forth in the above illustrative examples are expected to occur to those skilled in the art. Consequently only such limitations as appear in the appended claims should be placed on the invention.

What is claimed:

1. A method of treating a patient suffering from non-alcoholic steatohepatitis (NASH) comprising administering to said patient a therapeutically effective amount of cysteamine or a pharmaceutically acceptable salt thereof, or cystamine or a pharmaceutically acceptable salt thereof.

2. A method of treating a patient suffering from non-alcoholic steatohepatitis (NASH) comprising administering to said patient a therapeutically effective amount of a composition comprising cysteamine, or a pharmaceutically acceptable salt thereof.

3. The method of claim 1 or 2, wherein the total daily dose of cysteamine or salt thereof is about 0.5-2.0 g/m².

4. The method of claim 1 or 2, wherein the total daily dose of cysteamine or salt thereof is about 0.5-1.0 g/m².

5. The method of claim 1 or 2, wherein the cysteamine or salt thereof is administered at a frequency of 4 or less times per day.

6. The method of claim 5, wherein the cysteamine or salt thereof is administered two times per day.

7. The method of claim 1 or 2, wherein the cysteamine or cystamine or salt thereof is a delayed or controlled release dosage form that provides increased delivery of the cysteamine or cystamine to the small intestine.

8. The method of claim 7, wherein the delayed or controlled release dosage form provides a $C_{max}$ of the cysteamine or cystamine, or salt thereof, that is at least about 35% higher than the $C_{max}$ provided by an immediate release dosage form containing the same amount of the cysteamine or cystamine or salt thereof.

9. The method of claim 8, wherein the delayed or controlled release dosage form provides a $C_{max}$ at least about 50% higher than the $C_{max}$ of the immediate release dosage form.

10. The method of claim 8, wherein the delayed or controlled release dosage form provides a $C_{max}$ up to about 75% higher than the $C_{max}$ of the immediate release dosage form.

11. The method of claim 7, wherein the delayed or controlled release dosage form comprises an enteric coating that releases the cysteamine or cystamine or salt thereof product when the cysteamine or cystamine or salt thereof reaches the small intestine or a region of the gastrointestinal tract of a subject in which the pH is greater than about pH 4.5.

12. The method of claim 11, wherein the enteric coating comprises a coating selected from the group consisting of polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC) hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters.

13. The method of claim 1 or 2, wherein the cysteamine or cystamine or salt thereof is administered orally.

14. The method of claim 1 or 2, wherein the cysteamine or cystamine or salt thereof is administered parenterally.

15. The method of claim 2, wherein the administering results in improvement in liver fibrosis compared to levels before administration of the cysteamine or salt thereof.

16. The method of claim 2, wherein the administering results in a reduction in fat content of liver.

17. The method of claim 2, wherein the administering results in a reduction in the incidence of or progression of cirrhosis.

18. The method of claim 2, wherein the administering results in a reduction in the incidence of hepatocellular carcinoma.

19. The method of claim 2, wherein the administering results in a decrease in hepatic aminotransferase levels compared to levels before administration of the cysteamine or salt thereof product.

20. The method of claim 2, wherein the administering results in a reduction in hepatic transaminase of between approximately 10% to 40% compared to levels before treatment.

21. The method of claim 2, wherein the administering results in a reduction in alanine anminotransferase levels in a treated patient to approximately 30%, 20% or 10% above normal ALT levels, or at normal ALT levels (≧40 iu/L).

22. The method of claim 2, wherein the administering results in a reduction in aspartate anminotransferase levels in a treated patient to approximately 30%, 20% or 10% above normal AST levels or to normal AST levels.

23. The method of claim 2, wherein the administering results in a reduction in serum ferritin levels compared to levels before treatment with the cysteamine or salt thereof product.

24. The method of claim 2, wherein the cysteamine or salt thereof is administered with a second agent useful to treat NASH.

25. The method of claim 2, wherein the patient is a child or adolescent.

* * * * *